(12) United States Patent
Lan et al.

(10) Patent No.: US 11,181,241 B1
(45) Date of Patent: Nov. 23, 2021

(54) SELF-BALLASTED UV LIGHT TUBE DEVICE AND LIGHT

(71) Applicant: SHENZHEN GUANKE TECHNOLOGIES CO., LTD, Shenzhen (CN)

(72) Inventors: Qing Lan, Shenzhen (CN); Shoubao Chen, Shenzhen (CN); Ligen Liu, Shenzhen (CN); Jiqing Yang, Shenzhen (CN)

(73) Assignee: SHENZHEN GUANKE TECHNOLOGIES CO., LTD, Shenzhen (CN)

( * ) Notice: Subject to any disclaimer, the term of this patent is extended or adjusted under 35 U.S.C. 154(b) by 0 days.

(21) Appl. No.: 17/104,191

(22) Filed: Nov. 25, 2020

(30) Foreign Application Priority Data

Sep. 30, 2020 (CN) .......................... 202022221431.4

(51) Int. Cl.
*F21K 9/278* (2016.01)
*F21S 8/04* (2006.01)
*A61L 2/10* (2006.01)
*F21Y 103/00* (2016.01)

(52) U.S. Cl.
CPC .............. *F21K 9/278* (2016.08); *F21S 8/043* (2013.01); *A61L 2/10* (2013.01); *F21Y 2103/00* (2013.01)

(58) Field of Classification Search
CPC ............. F21K 9/278; F21S 8/043; A61L 2/10
See application file for complete search history.

(56) References Cited

U.S. PATENT DOCUMENTS

| | | | | |
|---|---|---|---|---|
| 4,141,686 | A  * | 2/1979 | Lewis | A61L 2/10 250/436 |
| 7,192,160 | B2 * | 3/2007 | Reiff, Jr. | F21L 2/00 362/228 |
| 10,830,418 | B2 * | 11/2020 | Goza | A61L 2/26 |
| 2008/0298080 | A1 * | 12/2008 | Wu | G02B 6/001 362/555 |
| 2009/0196029 | A1 * | 8/2009 | Kurtz | H01J 5/54 362/221 |
| 2010/0102729 | A1 * | 4/2010 | Katzir | F21K 9/278 315/113 |
| 2010/0214779 | A1 * | 8/2010 | Kao | F21V 23/06 362/249.02 |
| 2014/0177203 | A1 * | 6/2014 | Novak | F21V 25/04 362/95 |
| 2017/0198896 | A1 * | 7/2017 | May | F21V 19/0085 |
| 2018/0199413 | A1 * | 7/2018 | Bovino | F21V 23/003 |
| 2020/0200366 | A1 * | 6/2020 | Goza | F21V 15/01 |
| 2020/0283320 | A1 * | 9/2020 | Blad | B01F 5/0615 |

* cited by examiner

*Primary Examiner* — Leah Simone Macchiarolo
(74) *Attorney, Agent, or Firm* — Maier & Maier, PLLC

(57) ABSTRACT

A self-ballasted UV light tube device and light includes a rod body, two light caps, a ballast and the first light tube; the rod body has a length direction from one end to the other end, the rod body is provided with a concave surface which is provided along the length direction; two light caps connect to two ends of the rod body and work with the concave surface to form the accommodating groove, each of the light caps is provided with a mounting hole corresponding to the accommodating groove and each of the light caps is provided with a contact pin on the side apart from the rod body; the ballast is provided on the rod body and/or the light cap, the ballast connects electrically to the contact pin of any of the light caps, and the first light tube is a UV light tube.

10 Claims, 6 Drawing Sheets

SELF-BALLASTED UV LIGHT TUBE DEVICE AND LIGHT

CROSS-REFERENCE TO RELATED APPLICATIONS

The present patent application claims benefit and priority to Chinese Application No. 2020222214314 filed on Sep. 30, 2020 which is hereby incorporated by reference into the present disclosure.

FIELD

The present invention relates to the technical field of lights, particularly to a self-ballasted UV light tube device and lights applying the self-ballasted UV light tube device.

BACKGROUND

Compared with UV LED lamp beads, UV light tube has higher UV conversion efficiency and stronger sterilization effect. Common UV light tubes cannot be used by directly being connected to municipal power, but need ballasts adjust current and/or voltage introduced into UV light tubes. Therefore, the light body should be provided in the area where UV light tubes are installed and the ballast should be provided inside the light, so that the UV light tube can be driven to illuminate. As a result, the light size is large, the structure of lights using a UV light tube is complex, the scheme cost is high and it is inconvenient in use. In another aspect, there are many specifications of UV light tubes, so a specification of UV light tubes should match a specific specification of light holder, causing complex assembly.

The foregoing content is only used for assisting in understanding the technical scheme of the application, but not means the acknowledgement of that the above content is the current technology.

SUMMARY

The main objective of the present invention is to provide a self-ballasted UV light tube device to simplify the structure of lights and improve the adaptability of lights.

To achieve the aforesaid objective, the self-ballasted UV light tube device provided by the present invention in the present invention comprises:

rod body, the rod body has a length direction from one end to the other end; the rod body is provided with a concave surface which is provided along the length direction;

two light cap, the two the light caps connect to two ends of the rod body and work with the concave surface to form the accommodating groove, each of the light caps is provided with a mounting hole corresponding to the accommodating groove and each of the light caps is provided with a contact pin on the side apart from the rod body;

a ballast provided on the rod body and/or the light cap and connecting electrically to the contact pin of any of the light caps; and the first light tube which is a UV light tube with both ends going through two the mounting holes respectively and connects to the ballast electrically.

In one embodiment of the present invention, the rod body connects to two the light caps to form a mounting cavity which connect to the mounting holes;

the ballast is provided in the mounting cavity.

In one embodiment of the present invention, the light cap comprises:

a shell connecting to one end of the rod body and provided with the mounting hole; and connecting part connecting to the surface of the shell apart from the rod body in a removable way and provided with the contact pin provided on the surface of the connecting part apart from the shell in a convex way.

In one embodiment of the present invention, the surface of the shell is provided with several convex parts, there is a space between two adjacent the convex parts to form a locating groove, the surface of the connecting part is provided with a limiting bar provided in any of the locating grooves;

and/or, the surface of the connecting part is provided with several sign scales; the surface of the shell is provided with indication signs provided corresponding to several the sign scales.

In one embodiment of the present invention, each of the shells comprises the end shell and the end cover, one end of the end shell connects to one end of the rod body in a fixed way, the other end of the shell connects to the end cover in a fixed way, and the end shell is provided with the mounting hole;

the end cover forms a whole with the connecting part.

In one embodiment of the present invention, the light cap is also provided with a locating cavity;

the self-ballasted UV light tube device also comprises a control circuit board provided in the locating cavity, connecting electrically to the ballast and provided with a microwave sensing module.

In one embodiment of the present invention, the control circuit board is also provided with a lamp bead;

the light cap is also provided with a light hole connecting the locating cavity, and the light hole is provided with a light guide body provided corresponding to the lamp bead.

In one embodiment of the present invention, the light cap is also provided with a limit block provided corresponding to the mounting hole.

In one embodiment of the present invention, two sides of the accommodating groove are provided with a snap slot; the self-ballasted UV light tube device comprises a reflector plate whose both sides are located in the snap slot and are overlapped on the concave surface.

The present invention also puts forward a light which comprises a mounting bracket and the self-ballasted UV light tube device. the mounting bracket is provided with a locating groove;

the body of the self-ballasted UV light tube device is provided in the locating groove in a removable way and connects electrically to the mounting bracket.

The technical scheme of the present invention adopts two the light caps connecting to both ends of the rod body and working with the concave surface to form the accommodating groove, adopts a body with two ends provided with a contact pin, the first light tube is provided in the accommodating groove, the ballast is provided on the rod body and/or the light cap, the ballast connects to the lead or mounting bracket via the contact pin to drive the first light tube to illuminate; In other words, the ballast can be provided on a rod body and/or in the light cap, or the ballast can be provided on a rod body and/or outside the light cap, the ballast connects to the contact pin via the lead and also connects electrically to the first light tube, so that specifications of the first light tubes can work with two the light caps and the rod body to form a specification of self-ballasted UV light tube device to realize the integrality and compatibility of the self-ballasted UV light tube device; in another aspect, the ballast is integrated in the self-ballasted UV light tube device to simplify the structure complexity of the mounting bracket and improve the assembly convenience of the self-ballasted UV light tube device. The technical scheme of the present invention integrates the first light tube of a small size and the ballast into a self-ballasted UV light tube device of a larger size to make the UV light tube directly connect electrically to municipal electricity for use. This self-ballasted UV light tube device in the present invention can be applied in kinds of existing illuminating lights conveniently, and is characterized by a concise structure, small volume, low cost, convenient installation and convenient maintenance.

BRIEF DESCRIPTION OF THE DRAWINGS

To better describe the technical schemes of the embodiments of present invention or prior art, a brief introduction of FIG. to be used in the descriptions of the embodiment or prior art is made hereby. Obviously, the attached drawing described below is only several embodiments of the present invention. For common technicians in this field, they can obtain other attached drawings. Based on these structures shown in the attached drawing without making additional creative endeavors.

The implementation, functional characteristics and advantages of the present invention will be further illustrated hereinafter in conjunction with the embodiments and drawings.

DETAILED DESCRIPTION

Combined with the attached drawing in the embodiments of the present invention, to clearly and completely describe the technical scheme of the embodiments of present invention. Obviously, only part of the embodiments of present invention (instead of all of the embodiment) are described here. Based on the embodiment for the present invention, all other embodiments acquired by the ordinary technicians in this field without creative endeavors, shall be in the protection scope of the present invention.

It should be noted that, if there is a directional indication (upper, lower, left, right, front, and rear, etc.) in the embodiments of the present invention, the directional indication is only used to explain the relative positional relationship, motion condition, etc. between the components in a particular position (as shown in the attached drawing), and if the particular attitude is changed, the directional indication is changed accordingly.

In addition, if there are descriptions relating to "first", "second" and the like in the embodiments of the present invention, such descriptions of "first", "second" and the like are for descriptive purposes only and are not to be construed as indicating or implying their relative importance or implying an indication of the number of indicated technical features. Therefore, a feature defined as "first" or "second" may explicitly or implicitly includes at least one of the features. In addition, the "and/or" as stated in the whole text should be understood as there are three paralleled schemes where Scheme A, or Scheme B or Scheme A and scheme B can be met at the same time (taking "A and/or B as an example"). Moreover, the technical schemes of the embodiments can be combined with each other, but shall be based on the realization of ordinary technical personnel in this field. When the combination of technical solutions is contradictory or cannot be realized, it shall be considered that the combination of the technical solutions does not exist or involved in the protection scope of the present invention.

Figure 1:
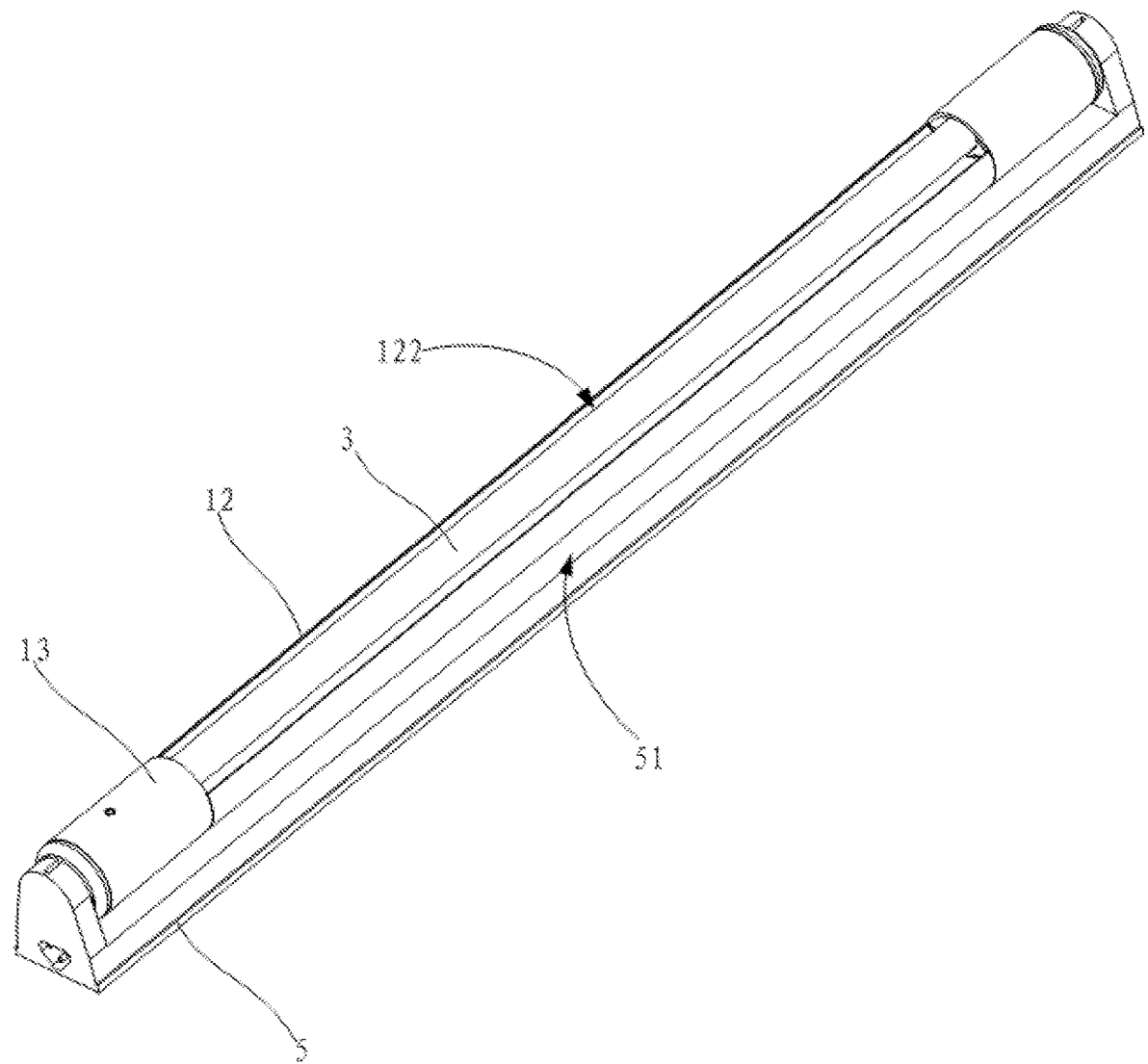
FIG. 1 is a schematic diagram showing the structure of an embodiment of lamp of this present invention.

The present invention provides a self-ballasted UV light tube device. Please refer to FIG. 1, it is a schematic diagram showing the structure of an embodiment of lamp of this present invention; Please refer to FIG. 2, it is a schematic diagram showing the assembly structure of lamp in FIG. 1; Please refer to FIG. 3, it is a schematic diagram showing the first cross-sectional structure of light in FIG. 1; Please refer to FIG. 4, it is a schematic diagram showing the second cross-sectional structure of light in FIG. 1; Please refer to FIG. 5, it shows a structural schematic diagram of light cap in FIG. 1; Please refer to FIG. 6, it shows a schematic structural drawing of the connecting parts of FIG. 5;

In the embodiment of the present invention, as shown in FIG. 1 and according to FIG. 2, FIG. 3, FIG. 4 and FIG. 5, the self-ballasted UV light tube device comprises: the rod body 12, two light caps 13, a ballast 2 and the first light tube 3; the rod body 12 has a length direction from one end to the other end, the rod body 12 is provided with a concave surface 123 which is provided along the length direction; two light caps 13 connect to two ends of the rod body 12 and work with the concave surface 123 to form the accommodating groove 122, each of light caps 13 is provided with a mounting hole 1311 corresponding to the accommodating groove 122 and each of light caps 13 is provided with a contact pin 11 on the side apart from the rod body 12; the ballast 2 is provided on the rod body 12 and/or the light cap 13 and connects electrically to the contact pin 11 of any one of light caps 13; the first light tube 3 is UV light tube with both ends going through two mounting holes 1311 respectively and connects electrically to the ballast 2.

In this embodiment, two light caps 13 connect to two ends of rod body 12 and work with the concave surface 123 to form the accommodating groove 122, both ends of the light cap body are provided with a contact pin 11, the first light tube 3 can be provided in the accommodating groove 122, the ballast 2 is provided on the rod body 12 and/or the light cap 13, the ballast 2 connects to the lead or the mounting bracket 5 via the contact pin 11 to drive the first light tube 3 to illuminate; In other words, the ballast 2 can be provided on a rod body 12 and/or in light cap 13, or the ballast 2 can be provided on a rod body 12 and/or outside light cap 13, the ballast 2 connects to the contact pin 11 via the lead and also connects electrically to the first light tube 13, so that specifications of the first light tubes 3 can work with two light caps 13 and rod body 12 to form a specification of self-ballasted UV light tube device to realize the integrality and compatibility of the self-ballasted UV light tube device; in another aspect, the ballast 2 is integrated in the self-ballasted UV light tube device to simplify the structure complexity of the mounting bracket 5 and improve the assembly convenience of the self-ballasted UV light tube device. The technical scheme of the present invention integrates the first light tube 3 of a small size and the ballast 2 into a self-ballasted UV light tube device of a larger size to make the UV light tube directly connect electrically to municipal electricity for use. This self-ballasted UV light tube device in the present invention can be applied in kinds of existing illuminating lights conveniently, and is characterized by a concise structure, small volume, low cost, convenient installation and convenient maintenance.

In the embodiment of the present invention, the light cap 13 can be an elongated structure with a certain length, the extension direction of the light cap 13 shares the same direction with the extension direction of the rod body 12, two light caps 13 connect to both ends of the first light tube 3 to compensate the length of the first light tube 3 to make the overall length of the self-ballasted UV light tube device meet the requirement of standard length of the light tube to make the self-ballasted UV light tube device be conveniently installed on the mounting bracket of existing LED illuminating lights or the mounting bracket of fluorescent tube lights used for illumination.

Figure 2:
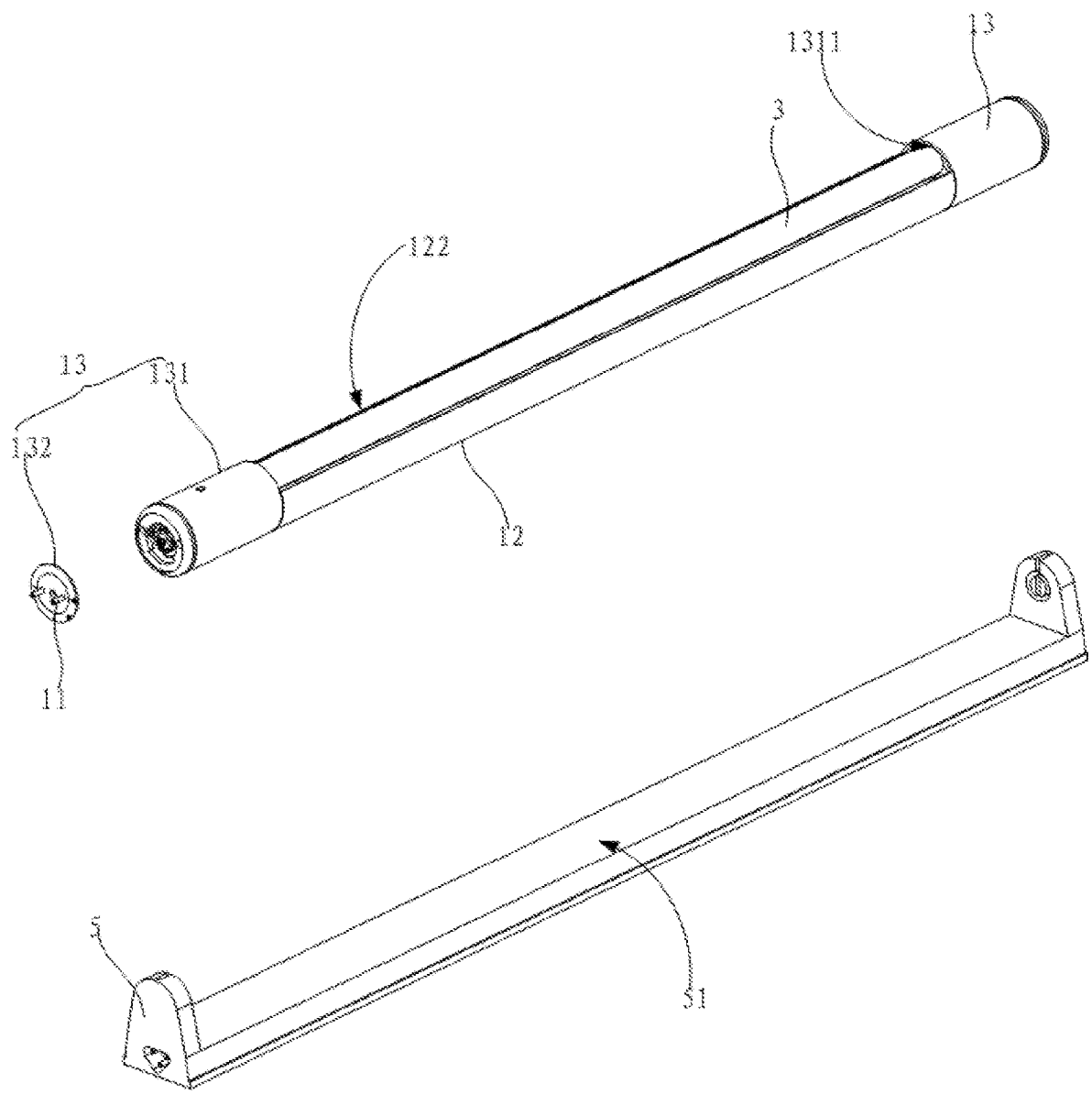
FIG. 2 is a schematic diagram showing the assembly structure of lamp in FIG. 1.

In one concrete embodiment of the present invention, as shown in FIG. 2, the rod body 12, two light caps 13, the ballast 2 and the first light tube 3 work to form an integral structure which can serve as a light tube; in other words, the rod body 12, two light caps 13, the ballast 2 and the first light tube 3 work to form the second light tube, contact pins 11 of two light caps 13 serve as the conductor for access of the second light tube to the power supply network. In another aspect, the contact pin 11 is of certain strength and can also serve as a locating structure to realize the objective of locating the second light body.

In one concrete embodiment of the present invention, the ballast 2 can be provided on the outer surface of rod body 12; or, the rod body 12 can be provided with a cavity inside, and the ballast 2 can be provided in the cavity of the rod body 12.

In one concrete embodiment of the present invention, the ballast 2 can be provided on the outer surface of any of light caps 13; or, any of light caps 13 is provided with a cavity, and the ballast 2 can be provided in the cavity of light caps 13.

In one concrete embodiment of the present invention, the ballast 2 can be provided on the outer surface of rod body 12 and light cap 13 to connect; or, the rod body 12 and the light cap 13 are provided with a cavity inside, and the ballast 2 is in the cavity.

In one concrete embodiment of the present invention, the ballast 2 and the first light tube 3 are connected electrically via lead.

In one concrete embodiment of the present invention, one light cap 13 is provided with two contact pins 11 which serve as two electrodes respectively and connect to the ballast 2 electrically.

In one concrete embodiment of the present invention, two light caps 13 is provided with at least one contact pin 11, and two contact pin 11 shall serve as two electrodes respectively and connect to the ballast 2 electrically.

In one concrete embodiment of the present invention, two ends of the first light tube 3 have two electrical connection ends which connect electrically to the ballast 2 respectively.

Figure 3:
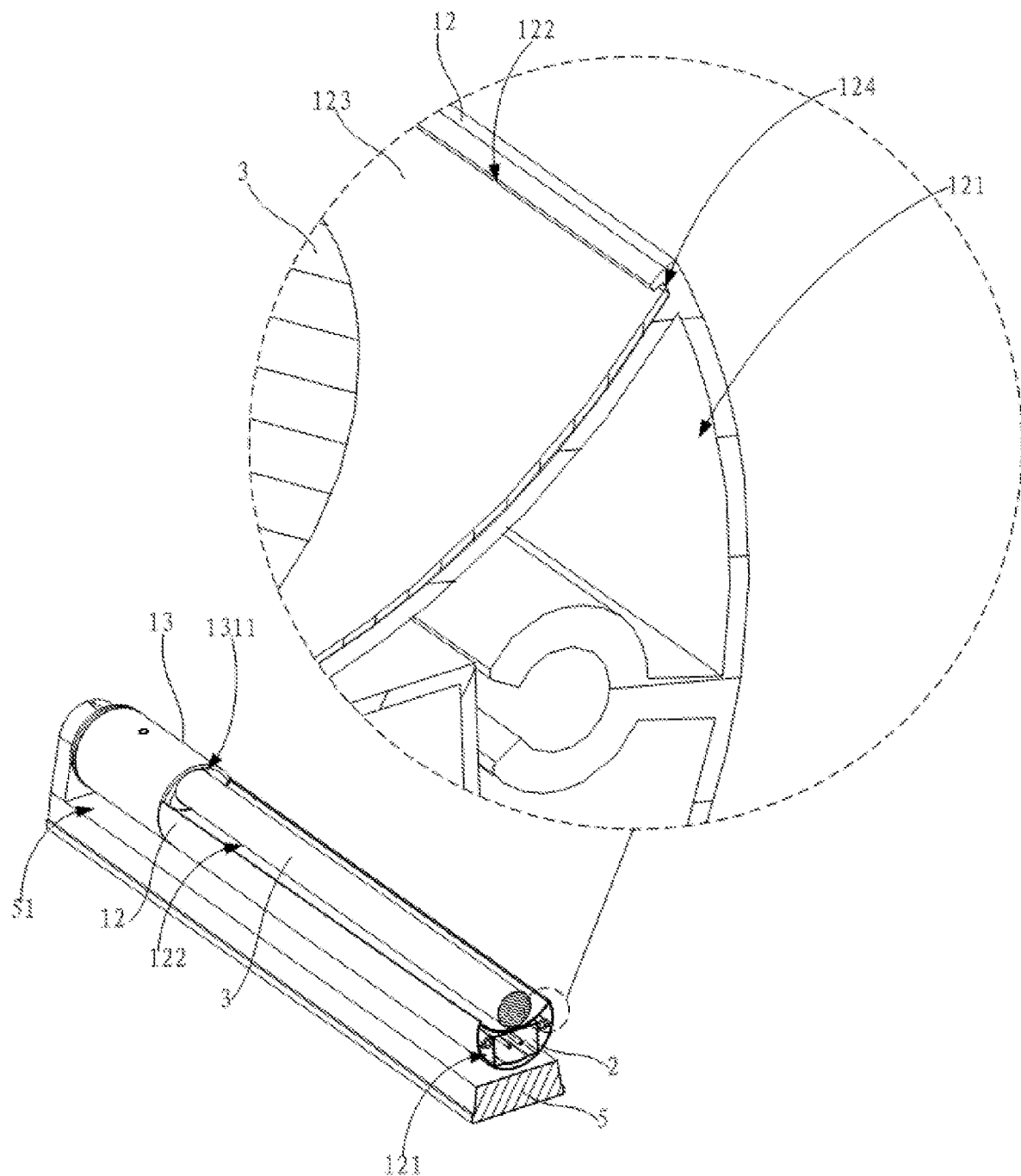
FIG. 3 is a schematic diagram showing the first cross-sectional structure of light in FIG. 1.
Figure 4:
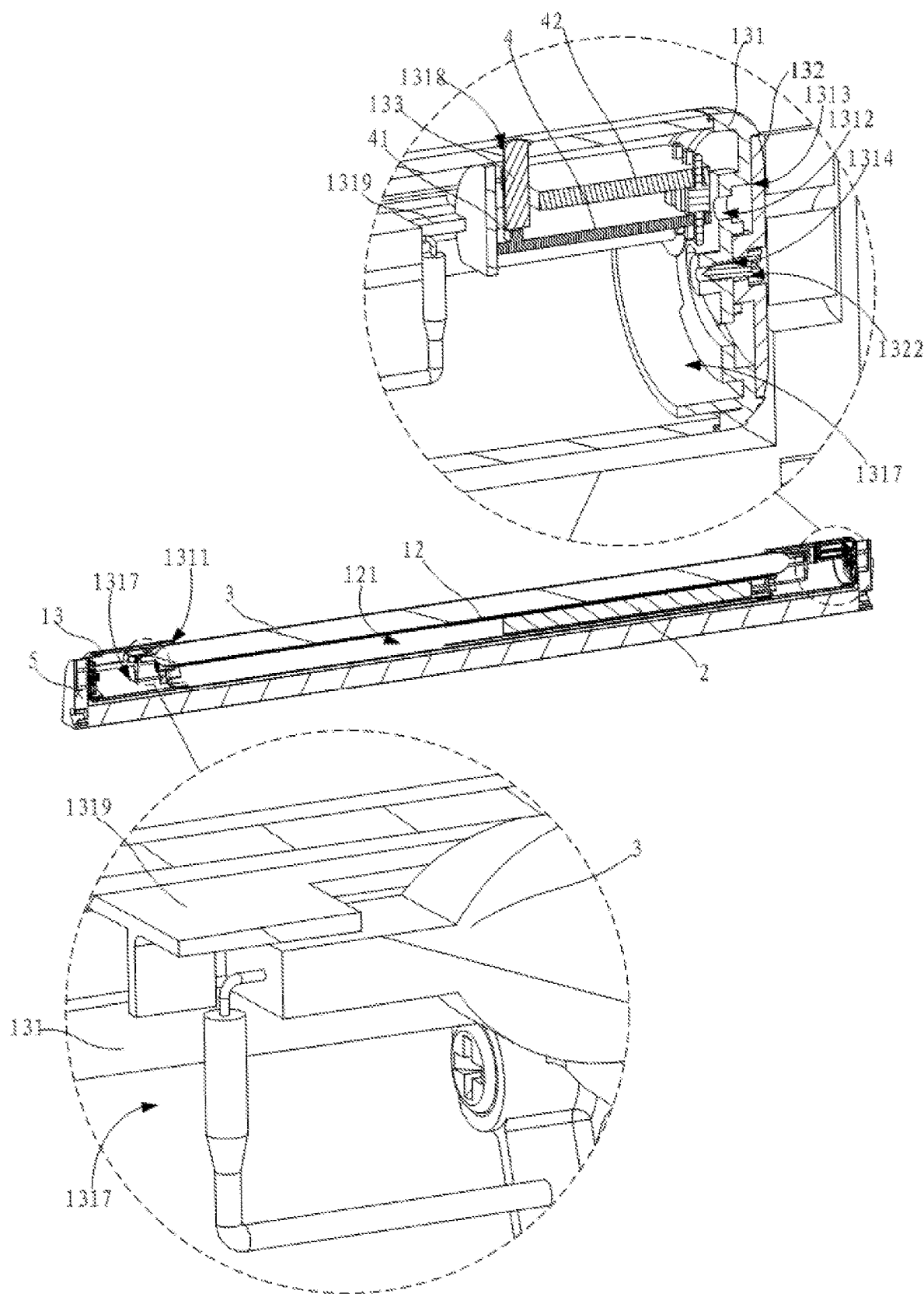
FIG. 4 is a schematic diagram showing the second cross-sectional structure of light in FIG. 1.

In one embodiment of the present invention, as shown in FIG. 3 and FIG. 4, the rod body 12 connects to two light caps 13 to form a mounting cavity 121 connecting mounting holes 1311; ballast 2 is in the mounting cavity 121.

In this embodiment, the rod body 12 is provided with the first cavity which is provided with the accommodating groove 122 at intervals; each of light caps 13 is provided with the second cavity, and the first cavity and the second cavity joint to form the mounting cavity 121. Wherein, the ballast 2 can be provided in the first cavity and/or second cavity optionally, preventing the ballast 2 being exposed to the outside space of the self-ballasted UV light tube device, preventing articles or environment changes in the outside space interfering work of the ballast 2 and improving the work reliability of the self-ballasted UV light tube device.

In one embodiment of the present invention, as shown in FIG. 3 and FIG. 4, each of light caps 13 has two contact pins 11.

In one embodiment of the present invention, as shown in FIG. 3 and FIG. 4, each of light caps 13 has two contact pins 11. Each of light caps 13 comprises: the shell 131 and the connecting part 132; the shell 131 connects to one end of the rod body 12, the shell 131 is provided with the mounting hole 1311; the connecting part 132 connects in a movable way to surface of the shell 131 apart from the rod body 12, the connecting part 132 is provided with contact pin 11, and the contact pin 11 is provided on the surface of the connecting part 132 apart from the shell 131 in a convex way. Wherein, the connecting part 132 can connect to the shell 131 through a snap joint; or, the connecting part 132 can connect to the shell 131 through a screw lock; or, the connecting part 132 and the shell 131 can be connected through a pin.

In this embodiment, the shell 131 and the connecting part 132 are connected in a movable way, the mounting position of the bracket of the connecting part 132 and the shell 131 can be adjusted. After the self-ballasted UV light tube device connects to mounting bracket 5 through contact pin 11, the inclination angle between the concave surface 123 on the rod body 12 and the mounting bracket 5 changes. In other words, the mounting position of the contact pin 11 on the connecting part 132 relative to the shell 131 can be changed through adjusting the mounting position of bracket of the connecting part 132 and the shell 131, so that the inclination angle between the concave surface 123 on the rod body 12 and the mounting bracket 5 is changed after the self-ballasted UV light tube device is installed onto the mounting bracket 5, and the light emitting angle formed by collaboration among the first light tube 3 and the rod body 12 and the light cap 13 can be adjusted conveniently.

Figure 5:
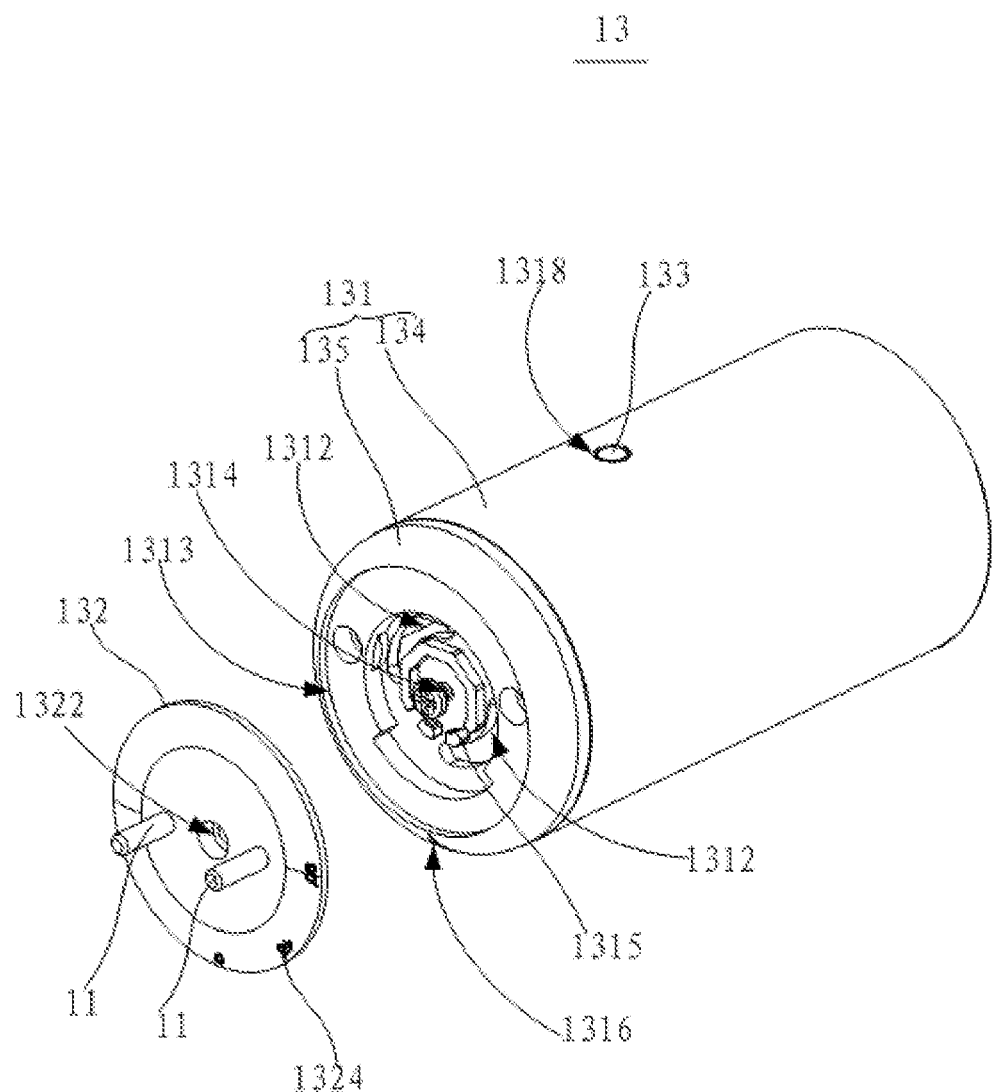
FIG. 5 is a schematic diagram showing the structure of light cap in FIG. 1.

In one concrete embodiment of the present invention, as shown in FIG. 3, FIG. 4 and FIG. 5, the shell 131 connects to one end of the rod body 12, and the shell 131 is provided with a mounting hole 1311 jointing the accommodating groove 122 and the wire hole 1312 jointing the mounting cavity 121; the connecting part 132 connects to the surface of the shell 131 apart from the rod body 12 in a rotatable way; the plug connects to the connecting part 132 and connects electrically to the ballast 2 via lead by passing through the wire hole 1312, one end of the light tube passes through the mounting hole 1311 and connects electrically to the ballast 2.

Figure 6:
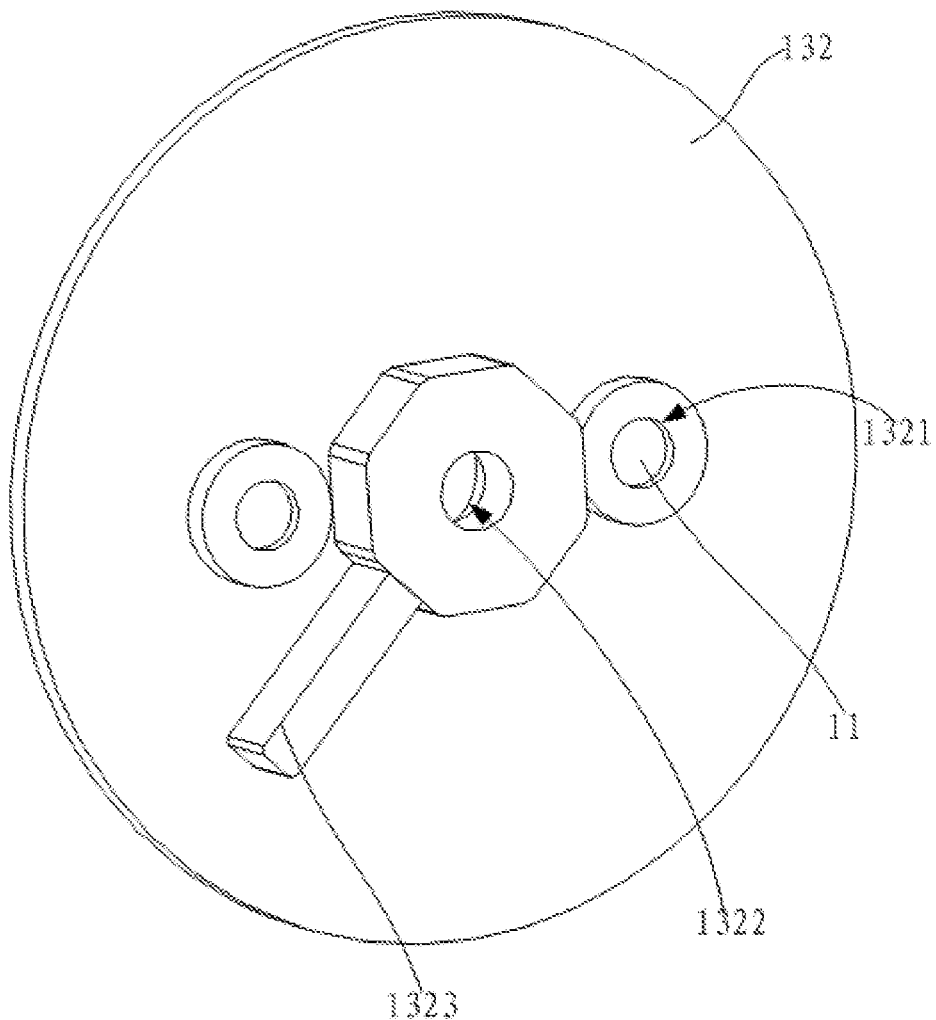
FIG. 6 shows a schematic structural drawing of the connecting parts of FIG. 5.

In one concrete embodiment of the present invention, as shown in FIG. 4, FIG. 5 and FIG. 6, the connecting part 132 is provided with the assembly hole 1321 corresponding to the wire hole 1312; The plug passes through the assembly hole 1321 and connects electrically to the ballast 2 via lead by passing through the wire hole 1312.

In one concrete embodiment of the present invention, the surface of the connecting part 132 facing the shell 131 can be provided with two metal sheets, and two plugs can connect to the corresponding metal sheet after connecting to the connecting part 132.

In one embodiment of the present invention, as shown in FIG. 5 and FIG. 6, the surface of the shell 131 is provided with several convex parts 1315, there is a space between two convex parts 1315 to form a locating groove, the surface of the connecting part 132 is provided with a limiting bar 1323 which is located in any of locating grooves. The connecting part 132 connects to the shell 131 to locate the limiting bar 1323 in the locating groove, so that the connecting part 132 and the shell 131 can be connected stably.

In one concrete embodiment of the present invention, as shown in FIG. 5 and

FIG. 6, the shell 131 is provided with a rotating tank 1313 whose bottom wall is provided with a wire hole 1312 and the first fixing hole 1314, the first fixing hole 1314 is in the middle of the rotating tank 1313 by having an interval with the wire hole 1312; the connecting part 132 is provided with the second fixing hole 1322 keeping an interval with the assembly hole 1321, fixing part connects to the inner wall of the first fixing hole 1314 by passing through the second fixing hole 1322 to make the connecting part 132 is provided in the rotating tank 1313 in a rotatable way.

In one embodiment of the present invention, as shown in FIG. 5, the surface of the connecting part 132 is provided with several sign scales 1324; the surface of the shell 131 is provided with indication signs 1316 which are provided corresponding to several sign scales 1324, so that users can intuitively see and adjust the assembly angle of the connecting part 132 and the shell 131.

In one concrete embodiment of the present invention, sign scale 1324 can be 30°, 60°, 90°, etc.

In one concrete embodiment of the present invention, indication sign 1316 can be arrow.

In one embodiment of the present invention, as shown in FIG. 5 and FIG. 6, each of shells 131 comprises an end shell 134 and an end cover 135, one end of the end shell 134 connects to one end of the rod body 12 in a fixed way, the other end of the end shell 134 connects to the end cover 135 in a fixed way, the end shell 134 is provided with a mounting hole 1311; the end cover 135 is provided by forming a whole with the connecting part 132. Wherein, the end cover 135 works with the end shell 134 to form the second cavity.

In this embodiment, the end cover 135 and the connecting part 132 form an integral structure to improve the overall stability of the self-ballasted UV light tube device.

In one embodiment of the present invention, as shown in FIG. 4, light cap 13 is also provided with a locating cavity 1317; wherein, the locating cavity 1317 can be another cavity by keeping an interval with the second cavity, or the second cavity joints the locating cavity 1317.

In one embodiment of the present invention, as shown in FIG. 4, the self-ballasted UV light tube device also comprises a control circuit board 4 provided in the locating cavity 1317, connecting electrically to the ballast 2 and provided with a microwave sensing module 42.

In this embodiment, control circuit board 4 is provided with a microwave sensing module 42, so that it can be judged whether there are people in the environment, so as to control work of the first light tube 3.

In one embodiment of the present invention, the control circuit board 4 is provided with a wireless module.

In one embodiment of the present invention, as shown in FIG. 4, the control circuit board 4 is provided with a lamp bead 41; light caps 13 are also provided with a light hole 1318 jointing the locating cavity 1317, the light hole 1318 is provided with a light guide body 133 which is provided corresponding to the lamp bead 41, so that users can judge the working state of the self-ballasted UV light tube device by viewing the light color guided by the light guide body 133.

In one embodiment of the present invention, the lamp bead 41 is used for emitting red, green and yellow light.

In one embodiment of the present invention, the light cap 13 is also provided with a limit block 1319 which is provided corresponding to the mounting hole 1311 and is against one end of the first light tube 3 to limit the position of the first light tube 3.

In one embodiment of the present invention, the limit block 1319 can be in the second cavity or the locating cavity 1317.

In one embodiment of the present invention, the limit block 1319 can be silica gel material or plastic material.

In one embodiment of the present invention, as shown in FIG. 3, both lateral sides of the accommodating groove 122 are provided with a snap slot 124; the self-ballasted UV light tube device comprises a reflector plate 14 whose both sides are located in the snap slot 124 and are overlapped on the concave surface 123. In other words, the two sides of rod body 12 are provided with snap slots 124 whose notch is on both sides of the accommodating groove 122.

In this embodiment, the reflector plate 14 can be metal material or plastic material, a mirror structure on the surface of the reflector plate 14 back onto the concave surface 123 is formed, so that UV rays generated by the first light tube 3 are reflexed into the outside environment and the use ratio of UV rays is improved.

The present invention also puts forward a kind of lamp. As shown in FIG. 1 and FIG. 11, the lamp includes the mounting bracket 5 and self-ballasted UV light tube device. The specific structure of the self-ballasted UV light tube device refers to the above embodiment. Because the lamp adopts all technical schemes of all above embodiments, at least all the beneficial effects of the technical scheme of the above embodiment are obtained. It will not be repeated in unnecessary details here. Wherein, the mounting bracket 5 is provided with a locating groove 51; the body is provided in the locating groove in a removable way and connects electrically to the mounting bracket 5.

Wherein, the mounting bracket 5 connects electrically to the power supply network. The contact pin 11 of the mounting bracket 5 corresponding to the light cap 13 is provided with an electrode which connects electrically to the contact pin 11 to supply power for the ballast 2.

the description is only the preferred embodiment of the present invention, and it is not for this reason that the patent scope of the present invention is limited. Any equivalent structural transformation made by using the description of the present invention and the attached drawings, or direct/indirect application in other related technical fields under the inventive concept of the present invention, is included in the patent protection scope of the present invention.

What is claimed is:

1. A self-ballasted UV light tube device comprising:
a rod body, the rod body has a length direction from one end to another end; the rod body is provided with a concave surface which is provided along the length direction; two light caps, the two the light caps connect to two ends of the rod body and work with the concave surface to form an accommodating groove,
each of the two light caps is provided with a mounting hole corresponding to the accommodating groove and each of the two light caps is provided with a contact pin on a side apart from the rod body; a ballast provided on the rod body and/or the light cap and connecting electrically to a contact pin of any of the two light caps; and
a first light tube which is a UV light tube with both ends going through two the mounting holes respectively and connects to the ballast electrically, wherein each of the two light caps comprises:
a shell connecting to one end of the rod body and provided with the mounting hole; and connecting part connecting to a surface of the shell apart from the rod body in a removable way and provided with the contact pin provided on the surface of the connecting part apart from the shell in a convex way.

2. The self-ballasted UV light tube device as claimed in claim 1, wherein a holder is movably connected with the housing and rotated relative to the housing.

3. The self-ballasted UV light tube device as claimed in claim 1, wherein the rod body connects to the two light caps to form a mounting cavity which connect to the mounting holes;
the ballast is provided in the mounting cavity.

4. The self-ballasted UV light tube device as claimed in claim 1, wherein the surface of the shell is provided with several convex parts, there is a space between two adjacent the convex parts to form a locating groove, the surface of the connecting part is provided with a limiting bar provided in any of the locating grooves;
and/or, the surface of the connecting part is provided with several sign scales; the surface of the shell is provided with indication signs provided corresponding to several the sign scales.

5. The self-ballasted UV light tube device as claimed in claim 1, wherein each of the shells comprises an end shell and an end cover, one end of the end shell connects to one end of the rod body in a fixed way, an other end of the shell connects to the end cover in a fixed way, and the end shell is provided with the mounting hole;
the end cover forms a hole with the connecting part.

6. The self-ballasted UV light tube device as claimed in claim 1, wherein the each of the two light caps is also provided with a locating cavity;
the self-ballasted UV light tube device also comprises a control circuit board provided in the locating cavity, connecting electrically to the ballast and provided with a microwave sensing module.

7. The self-ballasted UV light tube device as claimed in claim 6, wherein the control circuit board is also provided with a lamp bead;
each of the two light caps is also provided with a light hole connecting the locating cavity, and the light hole is provided with a light guide body provided corresponding to the lamp bead.

8. The self-ballasted UV light tube device as claimed in claim 1, wherein the light cap is also provided with a limit block provided corresponding to the mounting hole.

9. The self-ballasted UV light tube device as claimed in claim 1, wherein two sides of the accommodating groove are provided with a snap slot; and
the self-ballasted UV light tube device comprises a reflector plate whose both sides are located in the snap slot and are overlapped on the concave surface.

10. A light comprising:
a mounting bracket and the self-ballasted UV light tube device which as claimed in claim 1, the mounting bracket is provided with a locating groove;
the body of the self-ballasted UV light tube device is provided in the locating groove in a removable way and connects electrically to the mounting bracket.

* * * * *